United States Patent [19]
Weeks et al.

[11] Patent Number: 5,318,553
[45] Date of Patent: Jun. 7, 1994

[54] ABSORBENT PAD WITH DRYNESS CHARACTERISTICS

[76] Inventors: L. Jane Weeks, 114 Lakeside Way, Newnan, Ga. 30265; James A. Minetola, 314 Evian Way, Peachtree City, Ga. 30269; Timothy G. Wagner, 13019 SE Rivercrest Dr., Vancouver, Wash. 98684

[21] Appl. No.: 616,079

[22] Filed: Nov. 20, 1990

Related U.S. Application Data

[63] Continuation-in-part of Ser. No. 250,278, Sep. 28, 1988, abandoned.

[51] Int. Cl.⁵ .............................................. A61F 13/15
[52] U.S. Cl. .................................... 604/378; 604/358; 604/385.1
[58] Field of Search ................................ 604/374–380, 604/385.1, 381

[56] References Cited

U.S. PATENT DOCUMENTS

| | | | |
|---|---|---|---|
| 3,494,362 | 2/1970 | Burgeni | 128/290 |
| 3,771,525 | 11/1973 | Chapins | 604/381 |
| 3,865,111 | 2/1975 | Brooks | 604/378 |
| 3,995,638 | 12/1976 | Schaar | 604/385.1 |
| 4,014,338 | 3/1977 | Schaar | 604/378 |
| 4,041,950 | 8/1977 | Jones, Sr. | 604/375 |
| 4,103,062 | 7/1978 | Aberson et al. | 428/283 |
| 4,108,179 | 8/1978 | Schaar | 604/385.1 |
| 4,186,165 | 1/1980 | Aberson et al. | 264/112 |
| 4,486,192 | 12/1984 | Sigl | 604/382 |
| 4,531,945 | 7/1985 | Allison | 604/378 |
| 4,576,596 | 3/1986 | Jackson et al. | 604/380 |
| 4,627,848 | 12/1986 | Lassen et al. | 604/378 |
| 4,670,011 | 6/1987 | Mesek | 604/378 |
| 4,988,344 | 1/1991 | Reising et al. | 604/368 |
| 4,988,345 | 1/1991 | Reising | 604/368 |

FOREIGN PATENT DOCUMENTS

| | | | |
|---|---|---|---|
| 0522749 | 3/1956 | Canada | 604/378 |
| 0000593 | 2/1979 | European Pat. Off. | 604/378 |
| 2028627 | 12/1970 | Fed. Rep. of Germany | 604/378 |
| 2443667 | 3/1975 | Fed. Rep. of Germany | 604/378 |
| 2603491 | 8/1977 | Fed. Rep. of Germany | 604/378 |
| 0052241 | 11/1986 | Japan | 604/385.1 |
| 0050429 | 11/1909 | Switzerland | 604/378 |
| 0215237 | 9/1941 | Switzerland | 604/378 |
| 1018093 | 1/1966 | United Kingdom | 604/383 |
| 1149161 | 4/1969 | United Kingdom | 604/378 |
| 2233235 | 1/1991 | United Kingdom | 604/385.1 |

Primary Examiner—Randall L. Green
Assistant Examiner—Gina Gualtieri
Attorney, Agent, or Firm—Francis J. Bouda

[57] ABSTRACT

A unitary sanitary disposable absorbent incontinence pad has an elongated absorbent member between a pervious cover topsheet and an impervious backsheet. The absorbent member includes an absorbent batt which contains a combination of cellulose fibers and thermally-bondable fibers. A melt-blown web is superimposed on the batt. A portion of each lateral side of the batt is slit and turned inwardly toward the center of the batt to form a pair of fluid-barriers or dams, creating a fluid channel therebetween. The melt-blown web lies between the dams on top of the batt. Preferably the melt-blown web includes inturned side edges which may create a second channel therebetween. The assembly of batt and web are particularly effective for moving fluid longitudinally in said pad and preventing leakage along the sides of the pad.

6 Claims, 3 Drawing Sheets

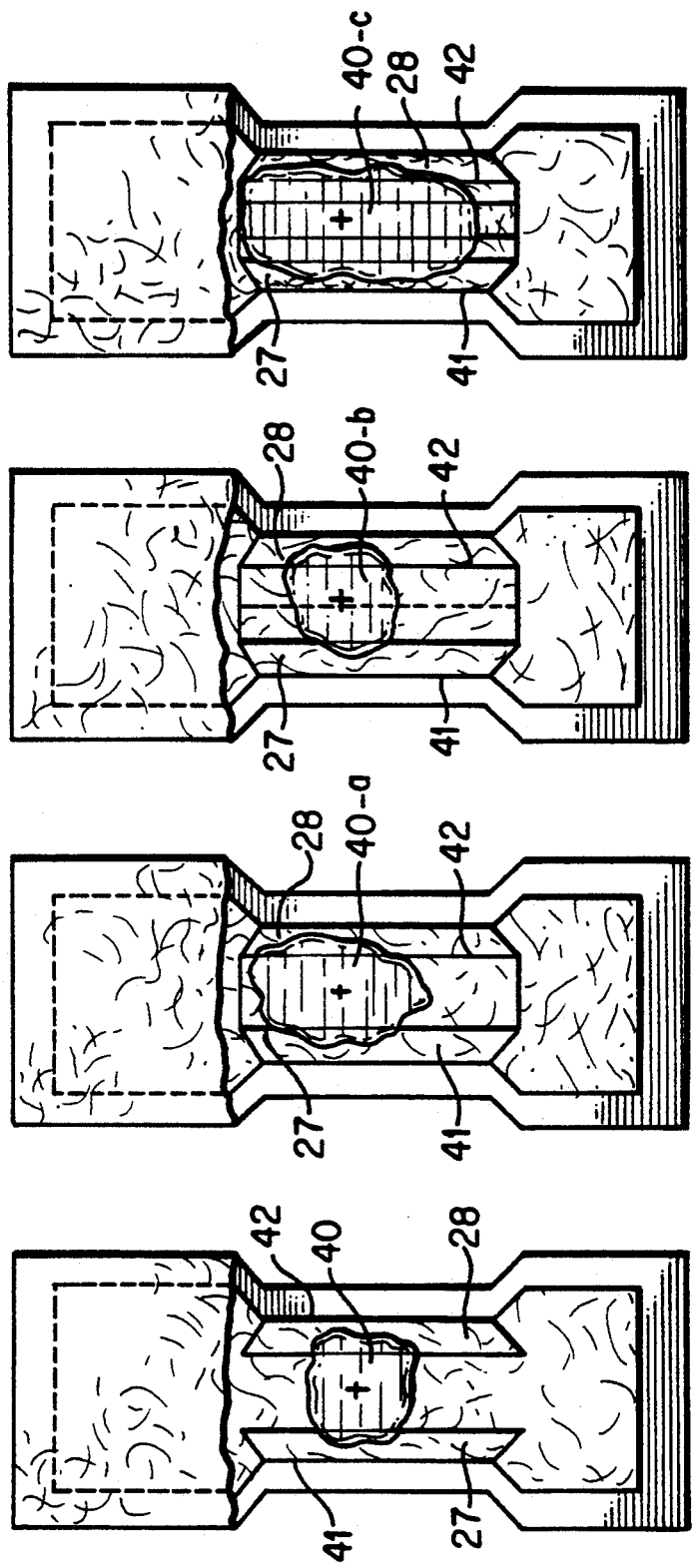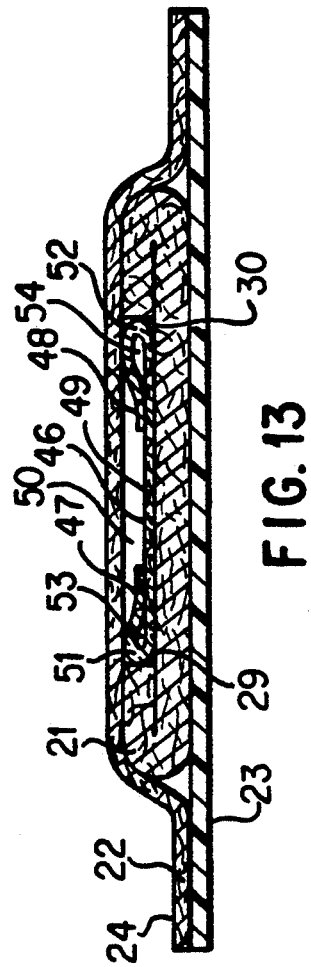

ABSORBENT PAD WITH DRYNESS CHARACTERISTICS

BACKGROUND OF THE INVENTION

This is a continuation-in-part of U.S. patent application Ser. No. 250,278, filed Sept. 28, 1988, now abandoned.

Disposable sanitary absorbent pads are not new, and sanitary napkins for female menstrual hygiene, baby diapers for infants, adult incontinence pads for elderly persons, and large, flat bed pads for institutional and hospital use have long been known.

The present invention, however, relates particularly to incontinence pads and baby diapers of a multi-layer construction similar to that shown in various issued U.S. patents.

Of particular interest is the Fridolph U.S. Pat. No. 2,122,417 which was issued on Jul. 5, 1938. In this particular infant's garment, as clearly shown in FIGS. 2 and 9, a portion of the absorbent material is slit and folded inwardly toward the center of the finished product so as to provide a triple layer absorbency mechanism in the center of the pad.

A similar structure is shown in the Foote U.S. Pat. No. 3,461,871, issued on Aug. 19, 1969, which also was constructed to provide additional absorbency in the center of the pad.

Additional prior art, directed to a similar construction to provide increased absorbency in the center of the pad, is shown in the McCurry U.S. Pat. No. 3,594,820 issued Jul. 27, 1971; Goughon U.S. Pat. No. 3,488,778 issued Jan. 13, 1970; and Kay U.S. Pat. No. 2,657,689 granted Nov. 3, 1953.

Each of these prior art references is characterized by having a central absorbent fluff-like batt of loosely-associated cellulose fibers, and all of them are directed to providing increased thickness in the center of the pad.

The present invention also distinguishes over the very early disposable one-piece baby diapers similar to that disclosed in the Duncan U.S. Pat. No. 3,180,335 (and its Re-Issue RE 26151), wherein, after the absorbent mat was formed as a rectangle and covered with a pervious sheet, the side edges were folded in to form a Z-shaped border which would create a pocket when the ends of the diaper were ultimately fanned outwardly and wrapped around the waist of the baby. Such "wing-folded" diapers were popular from the mid-1960's to the end of the 1970's, but have long since been replaced by the one-piece shaped elastic-leg diapers similar to the well-known brands on the market such as Procter & Gamble's "LUVS", Kimberly-Clark's "HUGGIES", and a variety of private label products. The earlier wing-folded diapers were deficient in that the "pocket" or retaining mechanism of the diaper ceased to function after the diaper was in use. The present invention includes the well-known pervious coverstock and impervious backsheet with an absorbent matt therebetween, but distinguishes over the earlier diapers in that the absorbent member is highly integrated, well-bonded, and stable in nature and construction with integral dams and channels formed in the absorbent member prior to covering with the pervious sheet material. The absorbent member also includes improved flow-spreading features.

SUMMARY OF THE INVENTION

The absorbent pad of the present invention can be distinguished over the prior art because it is constructed of a highly bonded matt (wherein the cellulose fibers are formed into a well-integrated matt which will not fall apart) by the use of thermo-bonding material mixed with the cellulose fibers and set by the application of heat during the manufacture of the pad.

Additionally, the matt contains a relatively significant percent by weight of superabsorbent material to increase the amount of fluid which can be retained in the batt under pressure.

Also, the present matt may include a porous melt-blown, or other porous nonwoven, web which aids in the distribution of the fluid in a lengthwise direction.

A further distinction is the construction of the pad in such a way that portions of the absorbent batt are slit and folded inwardly, to rest on top of the main portion of the matt, but deliberately folded inwardly short of the centerline of the pad so that there is no overlapping of the in-folded portions in the center of the pad.

This pad provides not only a highly absorbent center section, but a plurality of "side dams" which prevent the fluid (discharged into the center of the pad) from leaking outwardly over the side edges of the pad.

The pad of the present invention can also be distinguished over the pad shown in the co-pending patent application Ser. No. 250,278. The specific construction herein of the central absorbent portion (target area) has a distributor member in the channel between the "side dams" in order to utilize more effectively the full capacity of the absorbency of the pad and to improve the dryness characteristics thereof.

Therefore, an object of the present invention is to provide an absorbent pad with "side dams" to prevent sideward leakage of the fluid from the pad, with at least one channel to move the fluid lengthwise of the pad.

An additional object of the present invention is to provide a highly-integrated pad containing cellulose fibers, superabsorbent material, and a bonding mechanism to provide a comfortable, lightweight absorbent pad.

A still further object of the present invention is to provide a disposable sanitary absorbent pad with a distributor in the "target area" which provides a thin, light-weight and medically effective absorbent pad with improved dryness characteristics which minimize re-wet or "wet-back" of the fluid to the body of the wearer.

With the above and other objects in view, more information and a better understanding of the present invention may be achieved by reference to the following detailed description.

DETAILED DESCRIPTION

For the purpose of illustrating the invention, there is shown in the accompanying drawings a form thereof which is at present preferred, although it is to be understood that the several instrumentalities of which the invention consists can be variously arranged and organized and that the invention is not limited to the precise arrangements and organizations of the instrumentalities as herein shown and described.

In the drawings, wherein like reference characters indicate like parts:

Figure 4:
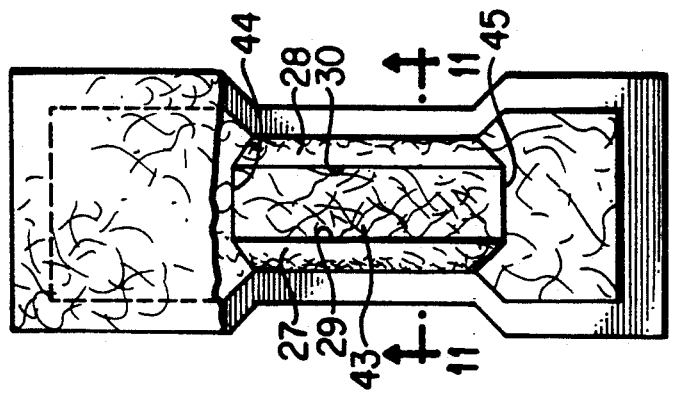
Figure 3:
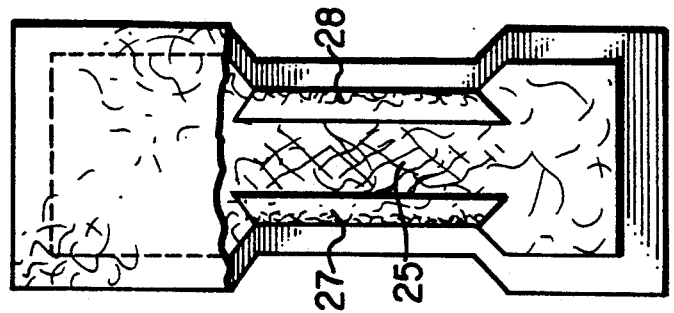
FIG. 3 is a plan view similar to FIG. 1 illustrating the matt without the embossed channels.

FIG. 4, similar to FIG. 3, shows a pad with a single ply melt-blown web superimposed on the absorbent core.

Figure 5:
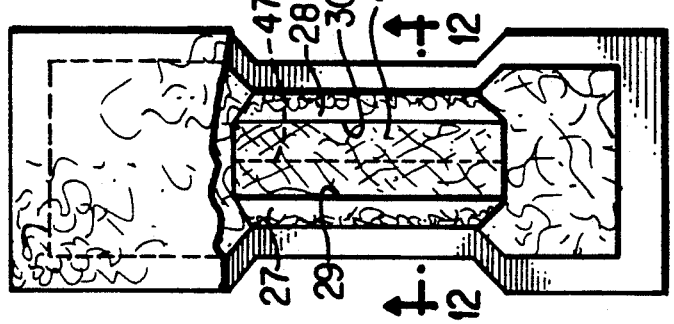

FIG. 5, similar to FIG. 4, illustrates a 2-ply melt-blown web superimposed on the absorbent core.

Figure 6:
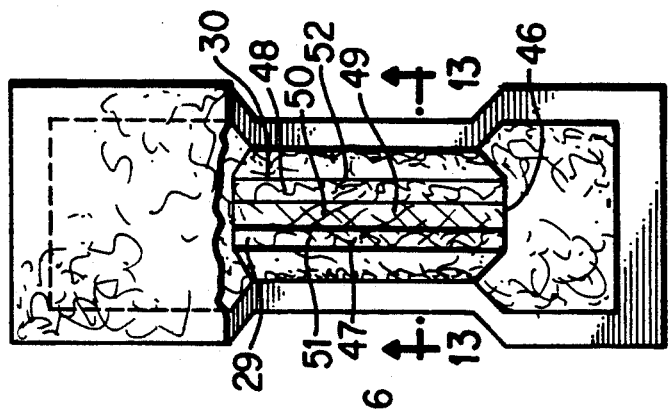

FIG. 6, similar to FIGS. 4 and 5, illustrates the use of a melt-blown web with inturned edges superimposed on the absorbent core.

FIG. 7 is a schematic view illustrating the fluid disposition on a pad similar to that shown in FIG. 3.

FIG. 8, similar to FIG. 7, shows the disposition of fluid on a pad of the type shown in FIG. 4.

FIG. 9, similar to FIGS. 7 and 8, illustrate the disposition of fluid on the pad similar to that shown in FIG. 5.

FIG. 10, similar to FIGS. 7, 8 and 9, shows the disposition of the fluid on the pad similar to that shown in FIG. 6.

Figure 11:
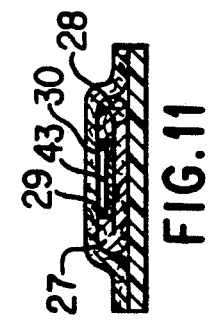

FIG. 11 is a vertical cross-section along lines 11—11 of the pad of FIG. 4.

Figure 12:
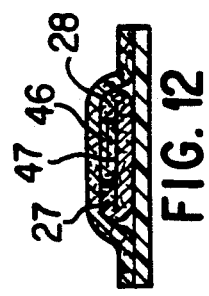

FIG. 12 is a vertical cross-section along lines 12—12 of the pad of FIG. 5.

FIG. 13 is a vertical cross-section along lines 13—13 of the pad of FIG. 6.

Figure 1:
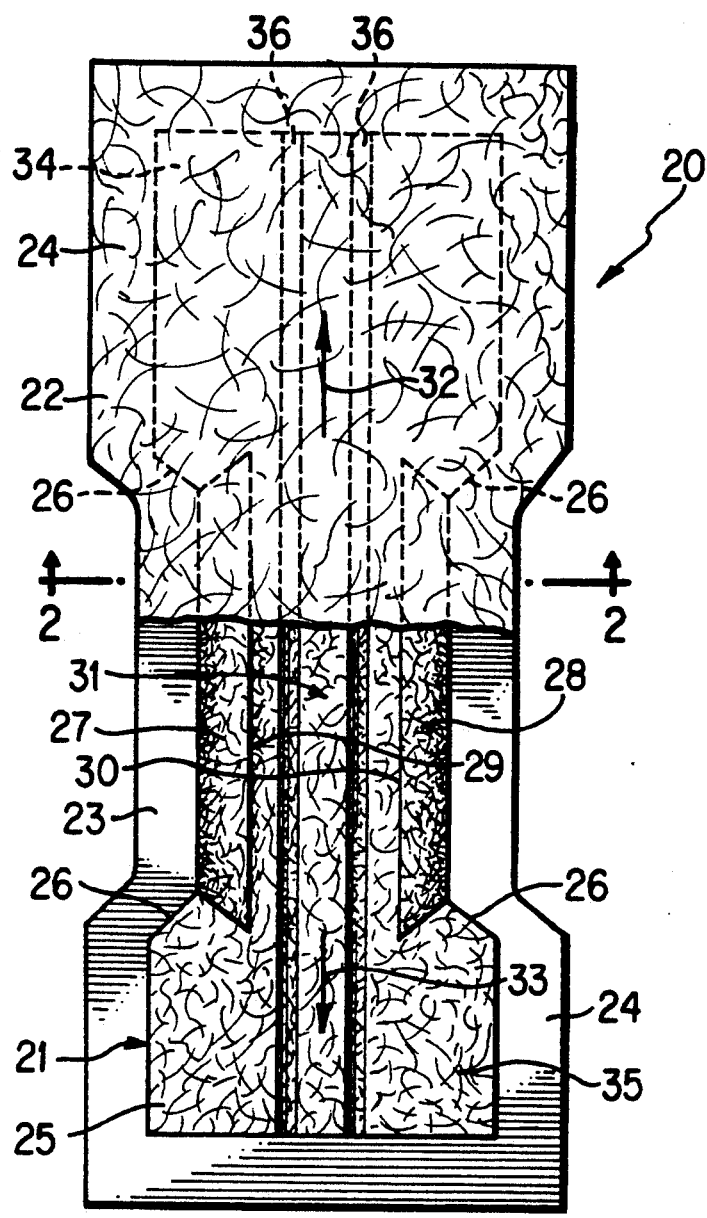
FIG. 1 is a top-plan view of one form of an absorbent pad of the present invention.

In FIG. 1, an absorbent pad 20 includes a highly absorbent, highly integrated absorbent matt 21, which is covered by a pervious web 22, which may be any one of the well-known coverstock materials made by a nonwoven process which can be thermally bonded, spun bonded, adhesively bonded, melt-blown, etc. Characteristic of such materials is a high loft, thru-air bonded coverstock comprised of bi-component fibers utilizing two or more polymer types in a sheath core relation. Those polymer types being polypropylene and polyester.

The underside of the pad is covered by a liquid-impervious web 23 which may be a thin, polyethylene sheet between 0.9 and 1.5 mils (25 to 30 microns) thick (all well-known in the art), designed to be soft and having little or no noise or "rattle" in use, but it may also be one of the newer "breathable back sheets" which is impervious to liquid, but may be pervious to moisture vapor.

The two webs 22 and 23 are bonded together around the perimeter 24 by heat-sealing, or by the application of hot-melt adhesive.

The absorbent matt 21 has a large body portion 25 and is preferably made of cellulose fibers bonded together by thermo-bondable fibers such as the "PULPEX" fibers developed by the Hercules Company of Wilmington, Del.

Figure 2:
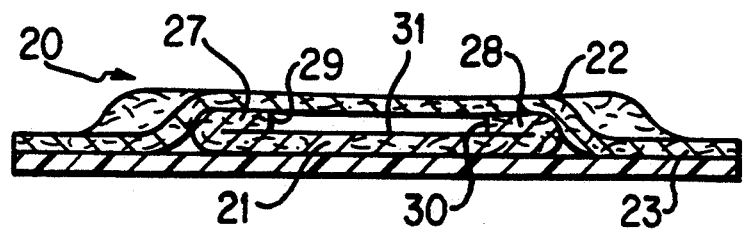
FIG. 2 is a cross-section taken generally along line 2—2 of FIG. 1.

Along each lateral side edge of the matt 21, a plurality of slits 26 are cut into the body-portion 25 so that lateral portions 27 and 28 may be folded inwardly upon the body portion 25 as is shown particularly in FIG. 2.

The longitudinal inner-edge 29 of the portion 27, and 30 of the portion 28, overlie only a relatively small portion of the body portion 25, and thus provide "dam-like" edges to create a channel 31 between the edges 29 and 30.

Thus when fluid is discharged against the pad between the in-folded members 27 and 28, it is generally retained in the channel 31 between the edges 29 and 30.

The absorbent matt 21 preferably contains a superabsorbent material which absorbs and retains the fluid.

As the fluid is discharged into the channel 31, it moves lengthwise of the pad, in the direction of the arrows 32 and 33, so that the end portions 34 and 35 of the pad may accept and retain the fluid therein.

One may, if desirable, provide a pair of embossed channels 36, which provide additional inducement for the fluid to move longitudinally in the pad rather than sideward. These embossed channels 36 may be enhanced by the provision of the "Burgeni" system disclosed in U.S. Pat. Nos. 2,952,260; 3,060,936 and 3,494,362.

Although the pads with the embossed channels shown in FIGS. 1 and 2 have proved more effective than flat pads without inturned edges or embossed channels, they are still not as desirable as the preferred embodiments shown in FIGS. 4-6 inclusive, and particular in FIG. 6.

In FIG. 3, we have shown a pad similar to that shown in FIG. 1, but without the embossed channels 36 therein. This pad includes the cut-and-fold lateral side portions 27 and 28, but with no other feature to collect the fluid discharged thereagainst, except the inherent absorbency of the integrated matt 25.

We have found from extensive studies and analyses that fluid discharged against the pad of this construction generally is retained within the central portion of the pad as shown at 40 in FIG. 7. With this construction, the fluid may flow beneath the inturned portions 27 and 28 but does not leak outwardly beyond the lateral margin 41 and 42.

The pattern 40 illustrated in FIG. 7 is typical of the fluid disposition of an insult (i.e. discharge) of nine milliliters (i.e. 9 grams or 9 cubic centimeters) through a coverstock web of 22 grams per sq. yard of 3 denier polypropylene staple fiber carded web material. The absorbent core was a thermo-bonded matt of 375 grams/sq. meter of approximately 47% cellulose fibers, 15% Hercules "PULPEX" synthetic fibers and 38% "NORSOCRYL B-65", a superabsorbent polymer, developed by the Norsolor Co. of Paris, France.

The absorbent body 25 was approximately 9.0 centimeters wide at its widest top and bottom portion. The central portion containing the inturned edges was approximately 12½ centimeters long, and the inturned edges were each approximately 1.5 centimeters wide, leaving a central channel of approximately centimeters in width.

The pattern 40 of the discharge as shown in FIG. 7 was approximately 5 centimeters wide by 6½ centimeters long.

Referring now to the embodiment shown in FIG. 4, we have provided an improved product, utilizing a single ply of one oz./sq. yard melt-blown web material made of polypropylene fibers. This web 43 lies between the edges 29 and 30 of the inturned portions of 27 and 28, extending longitudinally to the ends 44 and 45.

This hydrophobic melt-blown polypropylene material tends to slow the flow rate upon initial contact, then move the fluid in all directions, but when the fluid moving therealong reaches the edges 29 and 30, the movement is further retarded in a lateral or side-wise direction but continues to move longitudinally to provide a pattern which is generally slightly oval or elongated in the length-wise direction of the pad similar to that shown at 40-a in FIG. 8. When we have used a 2-ply layer of the porous hydrophobic melt-blown material, as shown at 46 in FIG. 5, the fluid disposition is more circular and similar to that shown at 40-b in FIG. 9. The 2-ply layer of FIG. 5 slows the flow rate more than the single layer of FIG. 4. The fluid moves in all directions at a slower rate before reaching the edges 29 and 30. However, the surface tension of the fluid interface with the 2-ply layer is greater than with the single layer or with thermo-bonded matt alone. Because of this increased surface tension, we have observed the fluid to "bead" and then "roll" either longitudinally or laterally. The "beading" becomes more evident with fluid insults greater than 9 ml.

The 2-ply melt-blown material may be made of 2 separate pieces or it may be a single piece with the edges turned inwardly beneath an upper portion, with the mating edges terminating along a line 47 as shown in FIGS. 5 and 12.

We believe that the interface (between the 2-plys of the melt-blown material) assists in creating a flow of the fluid in both a lateral and longitudinal direction before the fluid moves laterally a sufficient distance to come into contact with the edges 29 and 30 of the inturned portions 27 and 28. A typical disposition of the fluid (in a pad construction similar to that shown in FIG. 5) is the pattern 40-b shown in FIG. 9 which is approximately 5.8 centimeters long and 5.5 centimeters wide, with the insult of 9 milliliters terminating on the average approximately 0.5 centimeters short of the edges 41 and 42. However, we have also observed a tendency for the fluid insult to terminate unequal distances from the edges 41 and 42 for both FIGS. 8 and 9.

The most preferred embodiment of the invention is shown in FIG. 6, which provides a channel-in-channel construction of the pad. In this embodiment, the web 46 is wider than the dimensions between the edges 29 and 30 of the portions 27 and 28. The additional melt-blown lateral-edge material in the width direction is inturned along fold-lines 51 and 52, contiguous with the edges 29 and 30 of batt 25. This creates portions 47 and 48 which lie on top of the main bottom portion 49 of the web 46, thus forming a second channel 50 between and supplemental to the main channel 31 between the edges 29 and 30 of the inturned portions 27 and 28.

In the folding of the lateral edges 47 and 48 on top of the web 46, small tunnels 53 and 54 may be created which also enhance the longitudinal flow of the fluid and deter sidewise leakage into the side portions 27 and 28.

A typical pattern of an insult of 9 milliliters of fluid against a pad of the construction shown in FIG. 6 is that shown at 40-c in FIG. 10, wherein the fluid assumes a much more elongated pattern in the lengthwise direction of the pad, taking even more advantage of the absorbency in the lengthwise direction. More importantly, the lateral width of the fluid pattern is narrower on a more consistent basis than with FIGS. 7, 8, or 9. The narrower fluid pattern caused by the channel-in-channel construction creates a more comfortable product for the end-user. We believe this more longitudinal flow pattern occurs because the flow rate is retarded more in the lateral direction than in the longitudinal direction by the additional plies of 47 and 48 of melt-blown material positioned at the sides of the single ply 46. The pattern shown in FIG. 10 may be, for instance, 7.7 centimeters long and 5.0 centimeters wide and terminates from 0.8 to 1 centimeter short of the lateral edges 41 and 42 of the inturned portions 27 and 28.

Thus we have devised a structure for an absorbent incontinence pad which is an improvement in construction, design and efficiency over the prior art devices. It has been found that a pad of the construction shown in FIG. 6 with the channel-in-channel melt-blown sub-layer offers improved fluid flow control. Thus we can provide a pad which can be tailored for specific applications and uses and which offers an extra degree of effectiveness, ease of construction, efficiency and manufacture and economies over an absorbent sub-layer which has only a constant density.

Furthermore, we have found that the present construction using a lightweight open, non-wettable sub-layer (as contrasted to single or double plys of the same material) provides superior anti-leakage construction. Furthermore, we have found that the re-wetting characteristic (i.e., the prevention of the fluid flowing back through the coverstock into contact with the body) is better than or at least equal to that which uses either the single ply melt-blown construction shown in FIG. 4, or the 2-ply melt-blown construction shown in FIG. 5.

Furthermore, we have conducted additional tests with the pads constructed according to the designs shown in FIGS. 3, 4, 5 and 6 with discharges of larger quantities of fluid (i.e. insults of 60 milimeters) and have found that the re-wet characteristics, as well as the anti-leakage characteristics, are not as good in the pads of FIGS. 3, 4 and 5 as in a pad of the construction shown in FIG. 6.

Although not shown in the drawings, the outer side of the impervious plastic sheet 23 may include a plurality of adhesive strips, covered by a removable silicone cover sheet, to assist in holding the pad in place within the wearer's garment.

It is to be understood that the present invention may be embodied in other specific forms without departing from the spirit or special attributes hereof, and it is therefore desired that the present embodiments be considered in all respects as illustrative, and therefore not restrictive, reference being made to the appended claims rather than to the foregoing description to indicate the scope of the invention.

Having thus described the invention, what is claimed as new and desired to be protected by Letters Patent are the following:

1. An absorbent disposable incontinence pad having a previous coversheet, and impervious backsheet, and an absorbent matt therebetween, said matt including:

a highly integrated batt of fibers, said batt having an upper surface and containing cellulose fibers and thermally bondable polymer fibers, said batt having terminal ends defining a length, said batt having two lateral sides defining a width, a central portion between said side, and pair of slits disposed in each of said sides forming batt-portions which extend longitudinally between said slits, said batt-portions on each side being folded upwardly and inwardly to create folded layers which lie on the upper surface on each side of said central portion of the batt and have inturned edges which define a first channel beneath the pervious coversheet, said inturned edges of said folded layers providing abutments or dams adjacent the central portion of said batt to deter lateral movement of fluid deposited therebetween, a liquid-moving flow-spreading web layer disposed between said inturned edge of said batt-portions, said web having two lateral sides which are folded upwardly along said inturned edges of said first channel and inwardly to create folded layers which lie on an upper surface on each side of a central portion of said web, layer creating a second channel.

2. The absorbent pad of claim 1 wherein said web layer is hydrophobic, said hydrophobic web layer including includes melt-down fibers.

3. The absorbent pad of claim 1 wherein said web layer is hydrophobic, and is a multi-ply sheet.

4. The absorbent pad of claim 1 wherein said web layer is hydrophobic and has lateral edges said lateral edges are inturned along fold lines and a flat width greater than the distance between the inturned edges of said folded layers of said batt.

5. The absorbent pad of claim 4 wherein the fold lines of said hydrophobic web layer are in contact with the inturned edges of said folded layers of said batt-portions.

6. The absorbent pad of claim 5 wherein small tunnels (53), (54) are formed along fold lines.

* * * * *